(12) United States Patent
De Boer et al.

(10) Patent No.: US 7,617,822 B2
(45) Date of Patent: Nov. 17, 2009

(54) DRY POWDER INHALER AND METHOD FOR PULMONARY INHALATION OF DRY POWDER

(75) Inventors: Anne Haaije De Boer, Drachten (NL); Paul Hagedoorn, Assen (NL); Henderik Willem Frijlink, Eelde (NL)

(73) Assignee: Rijksuniversiteit Groningen, Groningen (NL)

( * ) Notice: Subject to any disclaimer, the term of this patent is extended or adjusted under 35 U.S.C. 154(b) by 729 days.

(21) Appl. No.: 10/561,410

(22) PCT Filed: Jun. 16, 2004

(86) PCT No.: PCT/NL2004/000427

§ 371 (c)(1),
(2), (4) Date: May 11, 2006

(87) PCT Pub. No.: WO2004/110538

PCT Pub. Date: Dec. 23, 2004

(65) Prior Publication Data

US 2006/0237010 A1    Oct. 26, 2006

(30) Foreign Application Priority Data

Jun. 16, 2003   (EP)   .................... 03076883

(51) Int. Cl.
*B05D 7/14*    (2006.01)
*B65D 83/06*   (2006.01)
*A61M 15/00*   (2006.01)
*A61M 16/10*   (2006.01)
*A61M 15/08*   (2006.01)

(52) U.S. Cl. ............................ 128/203.15; 128/203.12; 128/203.24

(58) Field of Classification Search ............ 128/203.24, 128/203.15, 203.21, 203.12, 203.14, 203.19, 128/203.23, 203.25, 200.14, 200.21, 200.23, 128/200.24

See application file for complete search history.

(56) References Cited

U.S. PATENT DOCUMENTS 3,921,637 A    11/1975   Bennie et al.
3,948,264 A    4/1976    Wilke et al.

(Continued)

FOREIGN PATENT DOCUMENTS

EP    0 129 985    1/1985

(Continued)

*Primary Examiner*—Justine R Yu
*Assistant Examiner*—Colin Stuart
(74) *Attorney, Agent, or Firm*—Merchant & Gould P.C.

(57) ABSTRACT

A breath actuated dry powder inhaler, comprising a substantially disc shaped air circulation chamber for de-agglomeration of entrained powdered medicament using the energy of the inspiratory air stream. The chamber has a substantially circular or polygonal sidewall extending about a central axis between top and bottom walls of the chamber so that the height of the chamber is smaller than its diameter. A plurality of air supply channels disposed about the circumference of the chamber, which channels extend from joint or separate air inlets and which channels enter the chamber substantially tangentially to its sidewall. At least one of the supply channels extends through a powder dose supply region of the inhaler. The chamber further comprises an air outlet axially extending from a discharge opening in the centre of the top or bottom wall of the chamber and connects to a discharge channel that extends to a mouthpiece. The inhaler comprises at least one further air circulation chamber for de-agglomeration of entrained powdered medicament, the chambers being connected to the mouthpiece in parallel.

16 Claims, 12 Drawing Sheets

U.S. PATENT DOCUMENTS

| Number | Kind | Date | Inventor | Class |
|---|---|---|---|---|
| 3,971,377 | A | 7/1976 | Damani | |
| 3,991,761 | A | 11/1976 | Cocozza | |
| 4,147,166 | A | 4/1979 | Hansen | |
| 4,368,850 | A * | 1/1983 | Szekely | 239/333 |
| 4,627,432 | A | 12/1986 | Newell et al. | |
| 4,778,054 | A | 10/1988 | Newell et al. | |
| 4,811,731 | A | 3/1989 | Newell et al. | |
| 4,907,583 | A | 3/1990 | Wetterlin et al. | |
| 5,035,237 | A | 7/1991 | Newell et al. | |
| 5,070,870 | A * | 12/1991 | Pearce | 128/203.15 |
| 5,320,714 | A | 6/1994 | Brendel | |
| 5,415,162 | A | 5/1995 | Casper et al. | |
| 5,435,301 | A | 7/1995 | Herold et al. | |
| 5,483,954 | A | 1/1996 | Mecikalski | |
| 5,505,193 | A * | 4/1996 | Ballini et al. | 128/200.15 |
| 5,505,196 | A | 4/1996 | Herold et al. | |
| 5,575,281 | A | 11/1996 | Mecikalski | |
| 5,660,169 | A | 8/1997 | Källstrand et al. | |
| 5,829,434 | A | 11/1998 | Ambrosio et al. | |
| 5,881,719 | A | 3/1999 | Gottenauer et al. | |
| 5,921,237 | A | 7/1999 | Eisele et al. | |
| 6,029,663 | A | 2/2000 | Eisele et al. | |
| 6,102,035 | A | 8/2000 | Asking et al. | |
| 6,202,643 | B1 * | 3/2001 | Sladek | 128/200.23 |
| 6,286,507 | B1 | 9/2001 | Jahnsson | |
| 2002/0040713 | A1 | 4/2002 | Eisele et al. | |
| 2002/0129817 | A1 * | 9/2002 | Raul | 128/203.15 |
| 2002/0170560 | A1 | 11/2002 | Young et al. | |

FOREIGN PATENT DOCUMENTS

| Country | Number | Date |
|---|---|---|
| EP | 0 385 156 A1 | 9/1990 |
| EP | 0 404 454 A1 | 12/1990 |
| EP | 0 407 028 A2 | 1/1991 |
| EP | 0 424 790 A2 | 5/1991 |
| EP | 0 467 172 A1 | 1/1992 |
| EP | 0 469 814 A1 | 2/1992 |
| EP | 0 481 666 A1 | 4/1992 |
| EP | 0 558 879 A1 | 9/1993 |
| EP | 1 129 705 A1 | 9/2001 |
| EP | 1 172 122 A1 | 1/2002 |
| EP | 1 177 805 A1 | 2/2002 |
| GB | 1118341 | 7/1968 |
| GB | 1478138 | 6/1977 |
| GB | 2 041 763 A | 9/1980 |
| WO | 90/15635 | 12/1990 |
| WO | 92/04928 | 4/1992 |
| WO | 92/05825 | 4/1992 |
| WO | 93/09832 | 5/1993 |
| WO | 95/28192 | 10/1995 |
| WO | 96/22802 | 8/1996 |
| WO | 96/32978 | 10/1996 |
| WO | 98/20836 | 5/1998 |
| WO | 98/26827 | 6/1998 |
| WO | 98/34664 | 8/1998 |
| WO | 98/58695 | 12/1998 |
| WO | 99/27987 | 6/1999 |
| WO | 99/32180 | 7/1999 |
| WO | 99/33505 | 7/1999 |
| WO | 99/62495 | 12/1999 |
| WO | 01/72605 A1 | 10/2001 |
| WO | 02/00280 A2 | 1/2002 |
| WO | 02/00281 A2 | 1/2002 |
| WO | 02/05881 A1 | 1/2002 |
| WO | 03/000325 A1 | 1/2003 |

* cited by examiner

DRY POWDER INHALER AND METHOD FOR PULMONARY INHALATION OF DRY POWDER

The invention relates to a breath actuated dry powder inhaler wherein powdered medicament is de-agglomerated in an air circulation chamber using the energy of the inspiratory air stream.

Dry powder inhalers are used to deliver drugs via the respiratory tract. Such pulmonary drug delivery is not only advantageous in treatment of disorders of the lungs, but is also advantageous for many other types of treatment that conventionally includes oral or parenteral administration of medicine.

Advantages of drug delivery via the pulmonary route over the oral route include rapid delivery to the site of action, reduced dose and the possibility to administer relatively large molecules, in particular molecules that exhibit poor or no bioavailability when administered through the oral route.

Advantages of drug delivery via the pulmonary route over the parenteral route include ease of administration and increased patient compliance.

Dry powder inhalers basically comprise a dose supply region for the powdered medicament, a mouthpiece section and a de-agglomeration area to de-agglomerate the powdered medicament. De-agglomeration is necessary to reduce powder particles from a particle size that allows the medicament to freely flow into and from a metering system to a particle size that allows adsorption of the medicament molecules contained in the powder by the alveoli, e.g. a size smaller than 5 µm, generally a size smaller than 3 µm. To facilitate flow of the powdered medicine, the drug particles are often carried in soft spherical pellets or on the surface of so called carriers. The pellets and/or carriers then form the powder particles that are de-agglomerated into smaller parts to free the drug particles.

De-agglomeration can be effectuated using an outside energy source, e.g. a motor driven impeller, but can also be effectuated using the energy of the inspiratory air stream.

Compared to dry powder inhalers that use an auxiliary power source to de-agglomerate the medicament, these so called breath actuated powder inhalers have the advantage of being independent from an energy source, which advantage can be used to increase reliability and simplicity of the design.

De-agglomeration under breath action can be effectuated in many ways, e.g. by passing the powder particles through helical pathways, but is preferably realised in an air circulation or "classifier" chamber.

Compared to other de-agglomeration principles, the air circulation or "classifier" chamber has the advantage of a high de-agglomeration efficiency, while further inhalation of particles of larger size can be prevented.

A breath actuated dry powder inhaler, comprising a substantially disc shaped air circulation chamber for de-agglomeration of entrained, "airborne", powdered medicament using the energy of the inspiratory air stream is disclosed in EP 1 129 705.

In the known inhaler, the chamber comprises an air outlet axially extending from a discharge opening in the centre of the top wall of the chamber, which air outlet connects axially to a discharge channel that extends to a mouthpiece. A sheath flow channel is provided coaxially around the discharge channel to provide a sheath flow exiting the mouthpiece. This sheath flow reduces mouth deposition of fine particles in the flow exiting the discharge channel.

Although highly efficient, disadvantage of this inhaler is that it is relatively bulky and is relatively costly to manufacture. Further, it is relatively difficult to inhale a large dose of powdered medicament in one inhalation.

The present invention generally aims to alleviate the disadvantages of the known inhaler, while maintaining its advantages.

In particular, it is an object of the present invention to provide a breath actuated dry powder inhaler with air circulation chamber that does not need a sheath flow.

Further, it is an object of the present invention to provide a breath actuated dry powder inhaler with air circulation chamber that has an alternative design, which inhaler can have a more compact and simplified construction.

Still further, it is an object of the present invention to provide a breath actuated dry powder inhaler with air circulation chamber, with which relatively large doses of medicament can be inhaled in one inhalation.

Thereto, the invention provides for a dry powder inhaler according the claims 1 and 18.

Further, the invention provides a breath actuated dry powder inhaler, comprising a substantially disc shaped air circulation chamber for de-agglomeration of entrained powdered medicament using the energy of the inspiratory air stream, the chamber having a substantially circular or polygonal sidewall extending about a central axis between top and bottom walls of the chamber so that the height of the chamber is smaller than its diameter, a plurality of air supply channels disposed about the circumference of the chamber, which channels extend from joint or separate air inlets and which channels enter the chamber substantially tangentially to its sidewall, at least one of the supply channels extending through a powder dose supply region of the inhaler, the chamber further comprising an air outlet axially extending from a discharge opening in the centre of the top or bottom wall of the chamber and connecting to a discharge channel that extends to a mouthpiece, wherein the discharge channel connects substantially transversely to the air outlet of the chamber.

By arranging the discharge channel to connect substantially transversely to the air outlet of the chamber, it is achieved that the flow from the air output to the discharge channel changes direction from coaxial to the chamber axis to transverse to the chamber axis. This way, the tangential component in the flow is decreased, so that mouth deposition is reduced without the need to provide a sheath flow.

In an elegant embodiment, the inhaler comprises a substantially planar housing, the chamber being disposed in the housing such that the central axis of the chamber extends transversely to the plane of the housing and the discharge channel being disposed in the housing such that it extends in the plane of the housing. This way, the inhaler can be of slim design, e.g. a flat disc, triangle or even a rectangle closely matching the size of a credit card. The mouthpiece may than be provided on an edge of the housing, while the discharge channel and the circulation chamber may extend in substantially parallel planes.

Advantageously, the powder dose supply area is formed by a sealed dose compartment containing a pre measured dose of powdered medicament, the dose compartment being included in the supply channel and blocking air passage through the channel until removal of the seal of the dose compartment. In particular, the sealed dose compartment may be a blister pocket sealed with a removable cover foil.

Preferably, the housing is built up of a stack of substantially planar elements. The planar elements can be provided with projections and openings that in the stack cooperate to form the flow passages of the inhaler. Such planar elements can be easily manufactured from thermoplastic material in an injection moulding process using relatively simple moulds. Assembly can be as simple as stacking the elements in the right order.

The sealed dose compartment may be included in the assembly, e.g. by including the blister in the stack with the cover foil extending out of the inhaler as a pull off portion. This way, the housing may form a disposable unit for a single dose. The seal may than also be used to cover the air inlet openings and/or the mouthpiece.

Alternatively, the housing may comprise a carrier carrying a plurality of sealed dose compartments, the compartments on the carrier being indexable relative to the supply area of the inhaler. This way, the housing may form a reusable unit or a disposable unit for a plurality of doses.

According to the invention, the breath actuated dry powder inhaler comprises at least one further air circulation chamber for de-agglomeration of entrained powdered medicament, the chambers being connected to the mouthpiece in parallel. This way, relatively large doses of medicament can be inhaled in one inhalation, while maintaining low respiratory resistance and high de-agglomeration efficiency.

It should be noted that the principle of connecting circulation chambers in parallel can also be used regardless of the orientation of the discharge channel relative to the air outlet, e.g. to form a breath actuated dry powder inhaler comprising at least one substantially disc shaped air circulation chamber for de-agglomeration of entrained powdered medicament using the energy of the inspiratory air stream, each chamber having a substantially circular or polygonal sidewall extending about a central axis between top and bottom walls of the chamber so that the height of the chamber is smaller than its diameter, a plurality of air supply channels disposed about the circumference of each chamber, which channels extend from joint or separate air inlets and which channels enter the chamber substantially tangentially to its sidewall, at least one of the supply channels of each chamber extending through a joint or separate powder dose supply region of the inhaler, each chamber comprising an air outlet axially extending from a discharge opening in the centre of the top or bottom wall of the chamber and connecting to a joint or separate discharge channel that extends to a single mouthpiece.

Preferably, two, three or four parallel chambers are provided. To allow equal flow through each chamber, preferably, the circulation chambers are substantially identical. For a flat housing, preferably the chambers are disposed in the same plane. Alternatively, to allow for a more bar like construction, at least two of the chambers are disposed in the parallel planes, the discharge openings of the chambers facing each other. The joint or separate discharge channels may than be disposed in a further plane, located between the parallel plane.

In case the chambers are connected to separate dose supply regions, the dose compartments may be connected to a common seal that is removed in one piece. Alternatively, the seals may be separate to allow a quantity to be inhaled in subsequent inhalations.

The invention also relates to a method for pulmonary inhalation, wherein dry powder medicament is inhaled from an inhaler and wherein the dry powder is de-agglomerated in a substantially disc shaped air circulation chamber in the inhaler using the energy of the inspiratory air stream, and wherein, under the action of the inspiratory air stream, the de-agglomerated medicament is axially discharged from the circulation chamber and is subsequently changed in direction to be fed in transverse direction towards a mouthpiece.

The invention also relates to a method for pulmonary inhalation wherein dry powder medicament is inhaled from an inhaler and wherein the dry powder is de-agglomerated in a plurality of substantially disc shaped air circulation chambers arranged in parallel in the inhaler using the energy of the inspiratory air stream, and wherein, under the action of the inspiratory air stream, the de-agglomerated medicament is axially discharged from the circulation chambers and is subsequently fed towards a mouthpiece.

Further advantageous embodiments are defined in the dependent claims.

The invention shall be elucidated using a number of preferred embodiments shown in a drawing. In the drawing is shown:

FIG. 1b a top plan view of the top plate for the inhaler of FIG. 1a;

FIG. 2c top plan view of the intermediate plate for the inhaler of FIG. 1a;

FIG. 1d a top plan view of the bottom plate for the inhaler of FIG. 1a;

FIG. 9a a top plan view of a disc shaped embodiment of the breath actuated dry powder inhaler, comprising a carrier carrying a plurality of sealed dose compartments, the compartments on the carrier being indexable relative to the supply area of the inhaler;

FIG. 9b a top plan view of a carrier for the embodiment of FIG. 9a;

FIG. 9c a top plan view of an intermediate plate for the embodiment of FIG. 9a.

The drawings show schematical representations of exemplary embodiments, which are given as non-limiting examples of the invention. In the drawing, for the various embodiments, identical or corresponding parts are denoted with the same reference numerals.

FIGS. 1a-d show a breath actuated dry powder inhaler 1, comprising two identical, substantially disc shaped air circulation chambers 2 for de-agglomeration of entrained powdered medicament using the energy of the inspiratory air stream. Each chamber 2 has a substantially circular sidewall 3 extending about a central axis 4 between substantially parallel top walls 5 (see also FIG. 4) and bottom walls 6 of the chamber 2 so that the height h of the chamber is smaller than its diameter d. A plurality of air supply channels 7 is regularly disposed about the circumference of each chamber 2, which channels 7 extend from separate air inlets and which channels enter the chamber 2 substantially tangentially to its sidewall 3. One of the supply channels 7 of each chamber 2 forms a powder channel 7a. The powder channels 7a originate from a joint channel 7b that extends through a joint powder dose supply region 8 of the inhaler 1. Each chamber 2 further comprises an air outlet 9 axially extending from a discharge opening 10 in the centre of the top wall 5 of the chamber 2 and that connects to a discharge channel 12. The discharge channels 12 merge into a joint discharge channel 12a that extends to a mouthpiece 13. The chambers 2 are thus connected to the mouthpiece 13 in parallel.

The discharge channel 12 connects substantially transversely to the air outlets 9 of each chamber. The axis of the mouthpiece 13 is orientated transversely to the central axes 4 the classifying chambers 2.

The inhaler 1 comprises a substantially planar housing 14 having the shape and size of a thick credit card, being constructed as a disposable unit. The chambers 2 are disposed in the housing 14 such that the central axes 4 of the chambers 2 extend transversely to the plane of the housing. The discharge channel 12, 12a is disposed in the housing 14 such that it extends in the plane of the housing. The mouthpiece 13 is provided on a peripheral edge 15 of the housing. The discharge channel 12, 12a and the circulation chambers 2 extend in substantially parallel planes. During inhalation, the mouthpiece 13 discharges an aerosol cloud of de-agglomerated powder particles entrained from the air recirculation chamber 2 in a direction parallel to the longitudinal axis 1 of the inhaler housing, while the axes of both classifying chambers 2 are perpendicular to the longitudinal axis 1 of the inhaler housing 14.

The housing 14 (see also FIG. 2) is built up of a stack of substantially planar elements 16. These elements 16 include a bottom plate 17, an intermediate plate 18 and a top plate 19. The planar elements are provided with projections 20 and openings 10 that in the stack cooperate to form the flow passages, in particular the chamber 2, the supply channels 7, the supply region 8 and the discharge channels 12, 12*a* of the inhaler 1. The top surface of the bottom plate 19 e.g. forms the bottom wall 6 of the chambers 2, and carries projections 20 that form the sidewalls 3. The chambers 2 are closed off by the bottom surface of the intermediate plate 18, forming the top walls 5 of the chambers 2. The intermediate plate 18 forms a division between a bottom plane in which the chambers 2 extend and a parallel top plane in which the discharge channel 12 extends. Discharge openings 10 in the intermediate plane 18 form a passage for air and entrained, de-agglomerated medicine particles exiting the chamber through air outlet 9 extending axially along axis 4. The bottom plate 19 comprises peripheral ridges 21, defining an aperture in which intermediate plate 18 is placed. Top plate 17 is stacked on top intermediate plate 18 and bottom plate 19. Top plate 17 is clamped under protrusions 22 protruding inwardly from the ridges 21, so that the contacting surfaces of the plates 16 cooperate in an substantially airtight manor.

The powder dose supply area 8 is in the embodiment of formed by a sealed dose compartment 23 containing a pre measured dose of powdered medicament. The dose compartment 23 is included in the joint supply channel 7*b* and is blocking air passage through the channel 7*b* until removal of the seal of the dose compartment. The sealed dose compartment 23 is shown as a blister pocket sealed with a removable cover foil 24. The blister 23 is included in the stack with the cover foil 24 extending out of the inhaler 1 as a pull off portion. As shown, the housing 14 forms a disposable unit for a single dose.

Referring to FIG. 2, a perspective view of an alternative embodiment of the inhaler of FIG. 1*a* is shown in assembled state with arrows indicating the air flow path. This embodiment contains a carrier 26 carrying three of dose compartments 23, the compartments on the carrier 26 being indexable relative to the supply area 8 of the inhaler 1.

A central air inlet 27 is provided on the rear 25 of the inhaler, generally opposite the mouth piece 13. The thickness of the top plate 17 is reduced locally, so that during inhalation through the mouth piece 13, air may enter between the top plate 17 and the intermediate plate 18, shown at arrow 1B to entrain powder from supply region 8 and carry it into the powder channel 7*b*.

In the embodiment shown, the dose compartments 23 can each subsequently be indexed to a position between additional air inlets 28 in the top plate 17 and the supply region 8. During inhalation, a further air flow at arrow 1A passes through the compartment and entrains the powder to the supply region 8. The embodiment shown further has entrances for a third air flow at arrow 1C for entraining any powder remaining in the supply region 8.

The flows 1A, 1B and 1C entrain the powder and carry it through joint powder channel 7*b* formed between the bottom 19 plate and intermediate plate 18 to a bifurcation of the powder channel 7*b*, where the air flow and the entrained powder is divided equally over two powder channels 7*a*, which each lead to a classifying chamber 2. In the embodiment shown in FIG. 1, only the flow 1B would be present, which would pass via aperture 11 in the intermediate plate 18 and trough the supply region 8 formed by the opened blister pocket. Preferably, the supply region comprises a ramp 29 at approximately ⅓ of the length of the blister pocket, so that the air flow through the channel 7*b* is forced through the interior of the blister pocket. The ramp may cooperate with the seal 24 to close the powder channel until the seal is removed.

A further air flow without powder, indicated at arrow 2, flows through rear supply channels 7 formed between the bottom plate 19 and the intermediate plate 18 to chambers 2. Yet another air flow without powder, indicated at arrow 3, flows from the front end of the housing 14 through an inlet 30 (visible in FIGS. 1*a* and 1*d*) formed between the top plate 17 and the intermediate plate 18, through a passage between the top plate and the intermediate plate, into front supply channels 7 (see also FIG. 3) of the chamber 2 formed between the intermediate plate 18 and the bottom plate 19. In the embodiment of FIG. 1, the front supply channels 7 are fed from the central air inlet 27 at the rear of the housing 14.

Powder particles are thus introduced into the chambers 2 by entrainment with air entering tangentially into the chambers 2 through the powder supply channels 7*a*. Additional air is supplied to the chambers 2 through supply channels 7, which also enter tangentially into the chambers. This way, a circular air flow is created in the chamber during inhalation. By distributing the supply channels evenly about the circumference of the chamber, the circulation of the flow in the chambers 2 is enhanced.

In the chambers 2, the particles are subjected to many different forces, including centrifugal forces due to the shape of the chamber, frictional forces exerted by the walls, impact forces due to collision of the particles with each other and with the sidewalls, as well as shear, drag and lift forces due to differences in speed between the particles and the air. Due to these forces, the powder particles break up. Finer particles are entrained with the air flow shown at arrow 4 exiting the chamber 2 axially through the air outlet 9 under the action of dominant drag forces.

Larger particles remain in the chamber under the action of dominant centrifugal forces until they break up. Relatively large particles that do not break up, e.g. sweeper crystals used to clean deposited particles from the walls of the chamber 2, can, if desired, be purged from the chamber after inhalation, e.g. through a purge opening in the bottom of the chamber (not shown). In case of a single use, disposable inhaler, the large particles can remain in the chamber. Such sweeper particles may e.g. be added to the powder formulation or may be preloaded in the chamber 2.

The air flow exiting the chamber axially though the air outlet flows into the discharge channels 12, which join into a joint discharge channel leading to the mouth piece 13.

As the discharge channels 12 each have a central axis 33 that extends perpendicularly to the central axis 4 of the associated chamber 2, the discharge 12 channel connects transversely to the central axis of the air outlet 9 of the chamber 2, which coincides with the central axis 4 of the chamber 2, it is achieved that the flow from the air outlet 9 to the discharge channel changes direction from coaxial to the chamber axis to transverse to the chamber axis before exiting the mouthpiece 13. This way, the tangential component in the flow is decreased, so that mouth deposition is reduced without the need to provide a sheath flow. This increases the efficiency of the actual delivery of medicine to the lungs.

To clean the discharge channel and to regulate the flow resistance of the inhaler 1, bypass channels 31 are arranged between the top plate 17 and the intermediate plate 18.

The powder in the dose compartment 23 may be the active or a formulation with the active being e.g. an unprocessed powder, a spherical pellet formulation, an adhesive mixture or a physical mixture, and/or a carrier excipient respectively a sweeper excipient, whereby the properties of the powder (formulation) may be adjusted to the specific properties of the classifier. A single dose of the active (with or without excipients) may be divided over a plurality of dose compartments pocket 23 for either simultaneous or subsequent inhalation. Each compartment may contain the same component or mixture, or may contain different components or mixtures. The compartments may be loaded from a metering apparatus in the housing, but are preferably pre-filled.

While the invention is shown in FIGS. 1 and 2 with a plurality of classifying chambers 2 arranged in parallel, it shall be clear to the skilled person that the invention can also be embodied in an inhaler 1 having a single classifying chamber 2 or a non-parallel arrangement of chambers 2. Further, it shall be clear that the inhaler 2 can also be embodied with classifying chambers in series, if desired in combination with a parallel arrangement.

It shall be clear to the skilled man that many variations are possible within the scope of the invention. With reference to the FIGS. 3-10, a number of these variations are discussed.

FIGS. 3*a-h* show top plan views of alternative embodiments for a bottom plate 19 for a breath actuated dry powder inhaler 1 having twin parallel circulation chambers 2. In the embodiments shown in FIGS. 3*a-f*, the classifier chambers 2 each have three supply channels 7, while FIGS. 3*g* and 3*h* show four supply channels 7.

In the embodiments shown in FIGS. 3*a* and 3*b*, the front supply channels 7 draw air from beneath the bottom plate 19. In the embodiments shown in FIG. 3*c* and FIGS. 3*e-h*, the air is supplied to the front supply channels 7 over the intermediate plate 18. In the embodiment shown in FIG. 3*d*, the air may be supplied through channels extending along the sides of the plate (not shown).

The number of channels 7 and their layout influences the air resistance, the speed in the circulation chamber 2, the accumulation of the drug in the chambers 2, the retention time of the particles in the powder and the maximum powder capacity per dose. Generally, the speed will increase if the number of supply channels is increased.

The shape of the circulation chambers 2 may be chosen to suit the formulation of the powder, e.g. substantially circular chambers (3*a*-3*e*, 3*g*) for pelletized powder particles and substantially polygonal chambers (3*f* and 3*h*) for carriers with adhesive particles.

In FIG. 3*f* and 3*h*, the classifier chambers 2 basically have the shape of a hexagon and an octagon, respectively. The sides of the octagon may have equal or different lengths in order to provide special acceleration sides and impaction plates with which carrier particles collide for effective fine drug particle removal. It is noted that the classifier chambers can have other shapes.

FIGS. 4*a-c* show cross sectional views of alternative chamber polygon embodiments for a breath actuated dry powder inhaler, based on FIG. 3*g* as an example. The diameter d of the classifier chamber and the diameter of the discharge hole 10 in the intermediate plate 18 of the classifier 2 may be varied relative to each other and relative to the size distribution of the carrier excipient in adhesive mixtures, in order to optimise the residence time inside the classifiers 2.

Referring to FIG. 4*b*, the discharge opening 10 of a classifier chamber 2 may be surrounded by a ring 32 projecting into the classifier chamber 2 in order to retain large carrier or sweeper particles. By adjusting the depth with which the ring 32 projects into the chamber 2, the size of the retained particles can be selected.

Referring to FIG. 4*c*, the bottom wall 6 and/or top wall 5 of the chamber 2 may be slightly conical or dome-shaped. The shape of the bottom and top wall also influence the retention time and retention efficiency (cut-off efficiency) of the chamber 2.

FIGS. 5 *a-d* top plan views of alternative embodiments for an intermediate plate 18 for a breath actuated dry powder inhaler 1 having twin parallel circulation chambers 2. The consecutive embodiments shown have an increasing number of bypass channels 31 connecting to the air outlet 9 of the chamber 2. The bypass channels 31 can be used to control the flow resistance of the inhaler 1. Further, the bypass channels 31 can be used to influence the shape of the aerosol cloud exiting the mouthpiece 13. In particular, a plurality of bypass channels 31 tangentially connecting to the air outlet 9 may further reduce mouth deposition.

The number and the orientation of the circulation chambers 2 can be varied.

FIGS. 6 *a-c* show top plan views of respectively a top plate 17, an intermediate plate 18 and a bottom plate 19 for a the breath actuated dry powder inhaler 1 having triple parallel circulation chambers. The circulation chambers 2 are linearly arranged in a plane along the longitudinal axis 1 of the inhaler housing 14.

FIG. 7*a* shows a top plan view of a bottom plate 19 of an alternative embodiment in which the axis through the mouth piece 13 extends at a sharp angle relative to the longitudinal axis 1 of the housing 14. In this embodiment, the joint powder channel 7*b* extends through two supply regions 8, each comprising a blister pocket 23. The housing of this embodiment comprises a central air inlet opening 27 that may be covered with a pull off cover, e.g. a foil. The pull off cover may be integrated with a removable foil 24 of the blister pocket 23.

FIGS. 7*b* and 8 show top plan views of respectively a top plate 17 and an intermediate plate 18 for a the breath actuated dry powder inhaler 1 having triple parallel circulation chambers 2, wherein the circulation chambers 2 are not arranged in line. As an alternative, the chambers 2 may be equally distributed about a central, parallel axis.

Figure 1A:
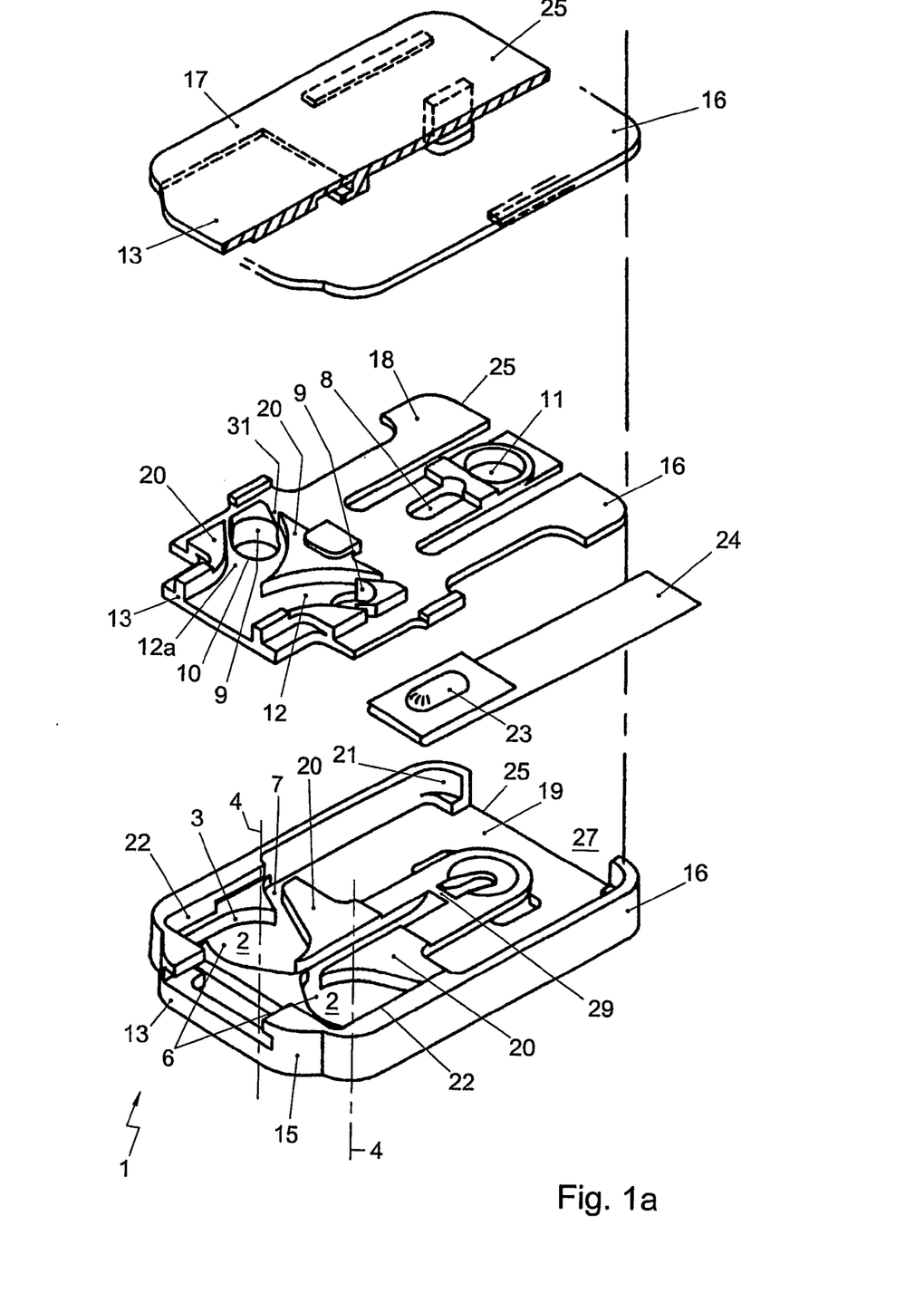
FIG. 1a an exploded view of a first embodiment of the breath actuated dry powder inhaler having twin parallel circulation chambers.
Figure 1B:
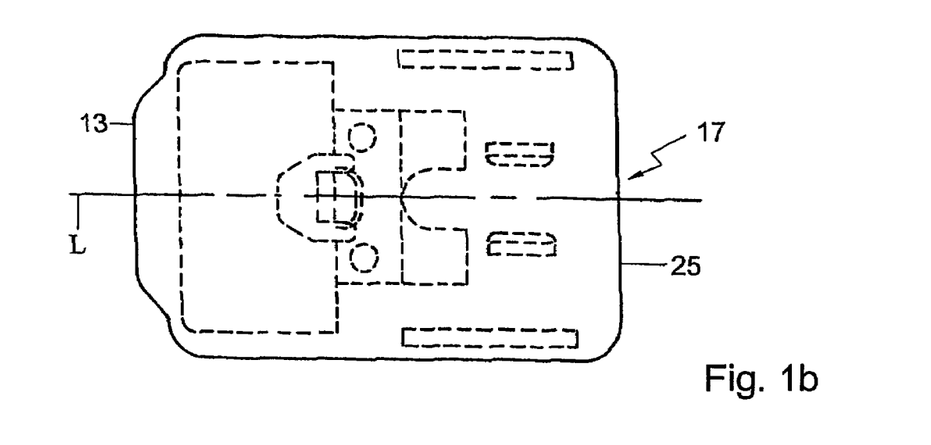
Figure 1C:
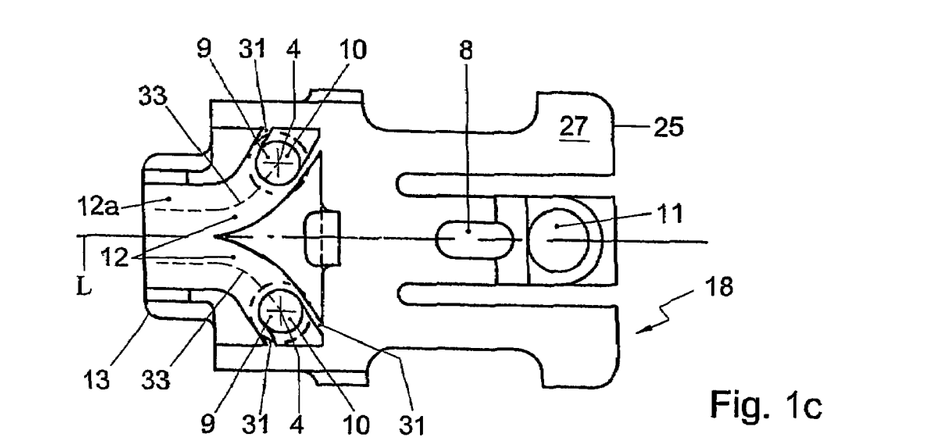
Figure 1D:
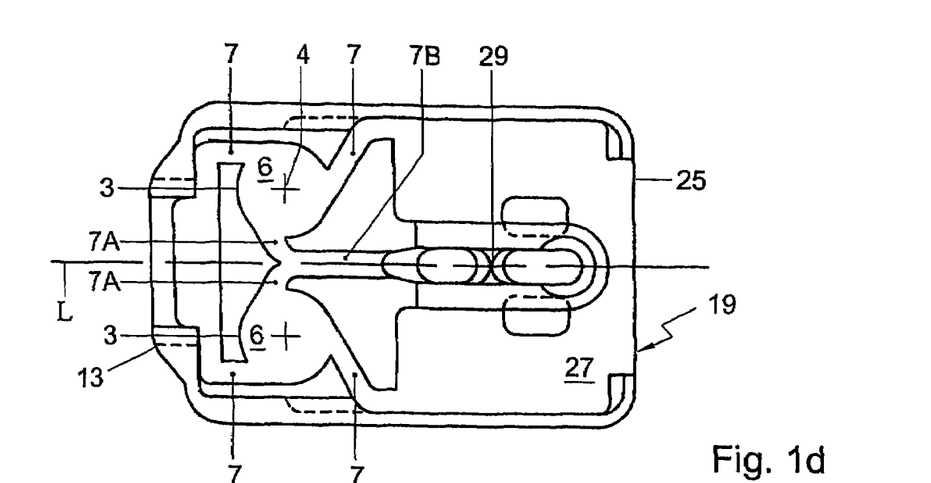
Figure 2:
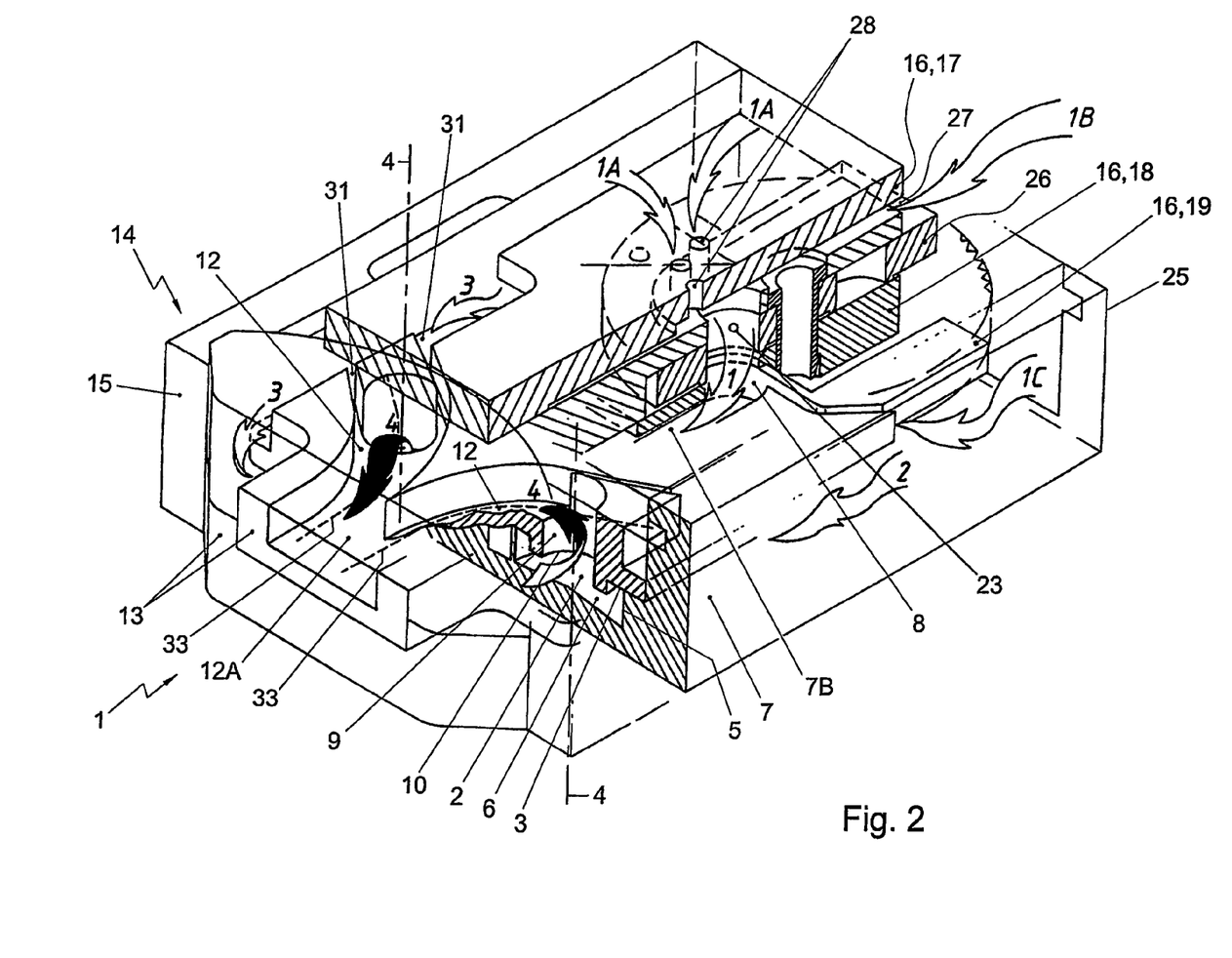
FIG. 2 a perspective view of an alternative embodiment of the inhaler of FIG. 1a in assembled state with arrows indicating the air flow path.
Figure 3A:
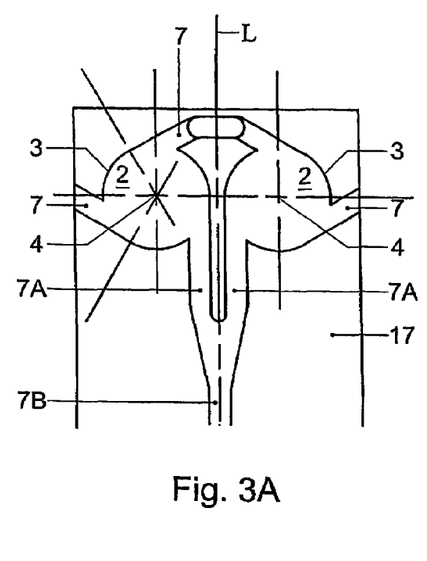
FIGS. 3a-h top plan views of alternative embodiments for a bottom plate for a breath actuated dry powder inhaler having twin parallel circulation chambers.
Figure 3B:
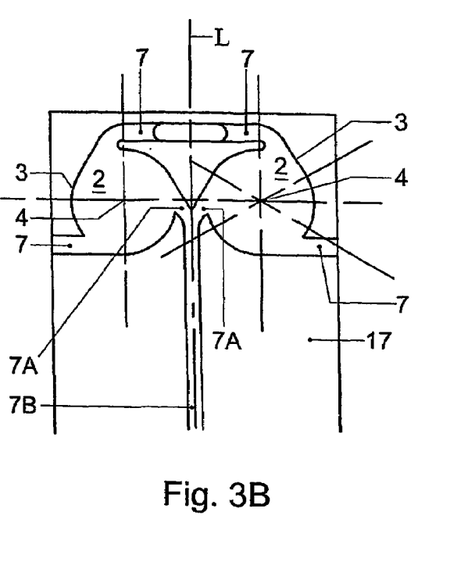
Figure 3C:
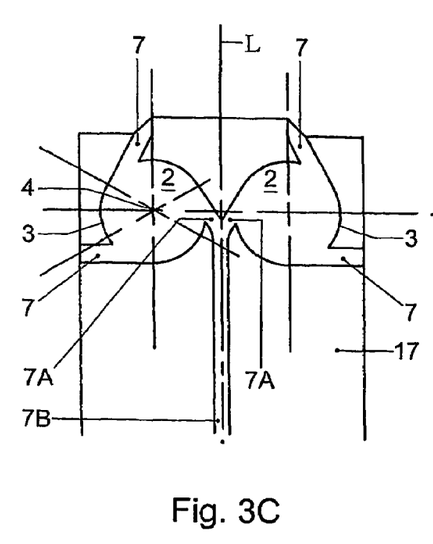
Figure 3D:
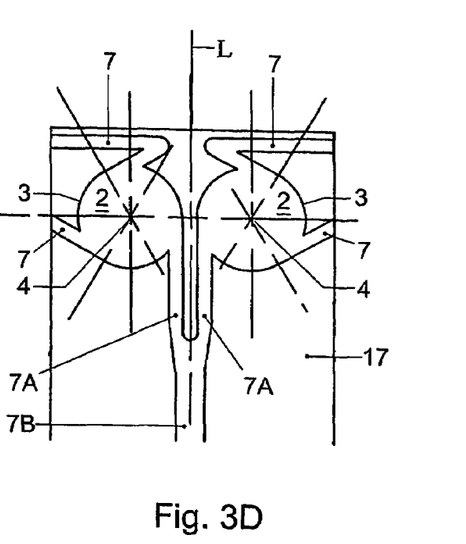
Figure 3E:
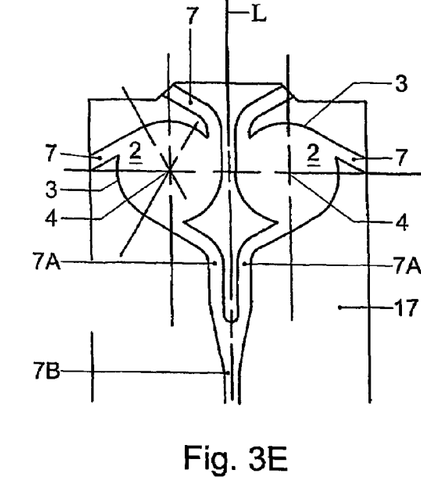
Figure 3F:
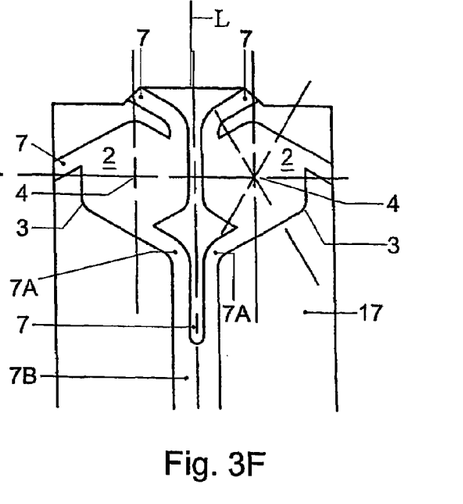
Figure 3G:
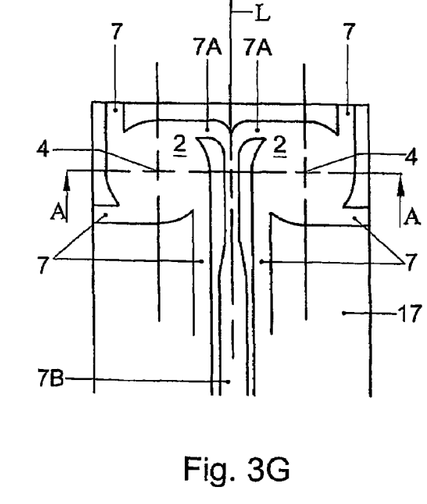
Figure 3H:
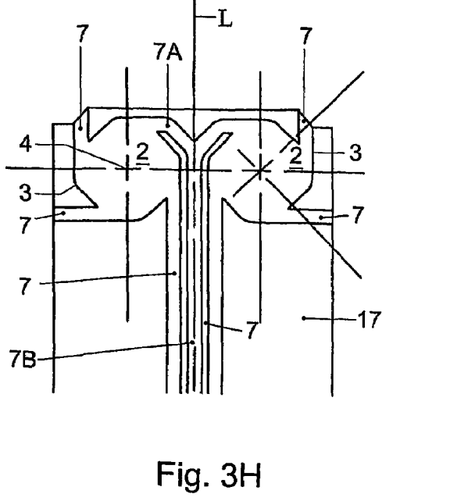
Figure 4A:
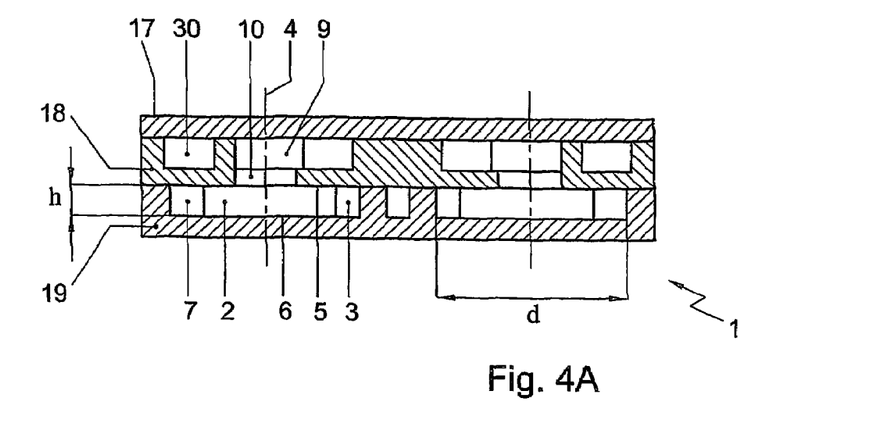
FIGS. 4a-c cross sectional views at section A-A of FIG. 3g of alternative chamber embodiments for a breath actuated dry powder inhaler.
Figure 4B:
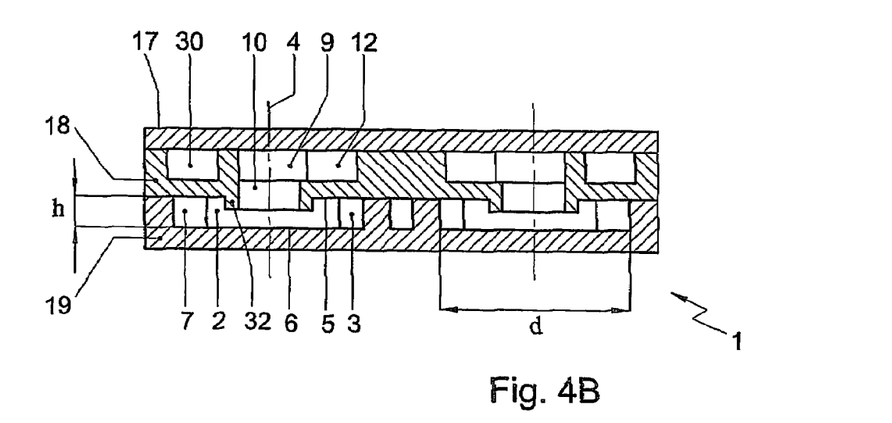
Figure 4C:
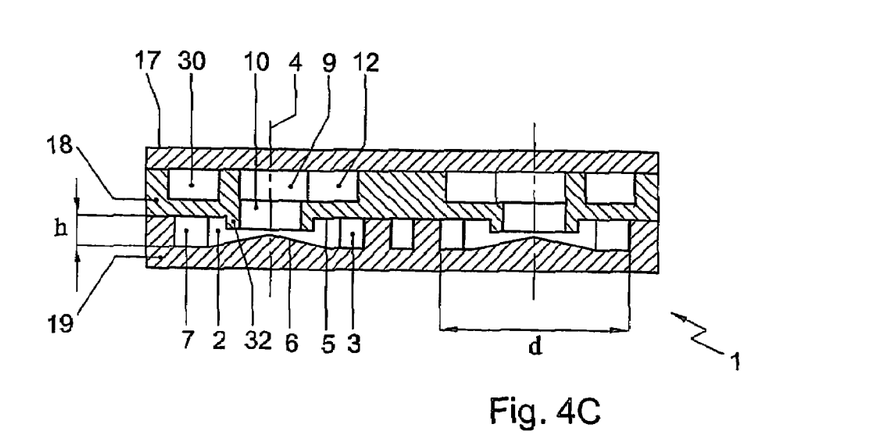
Figure 5A:
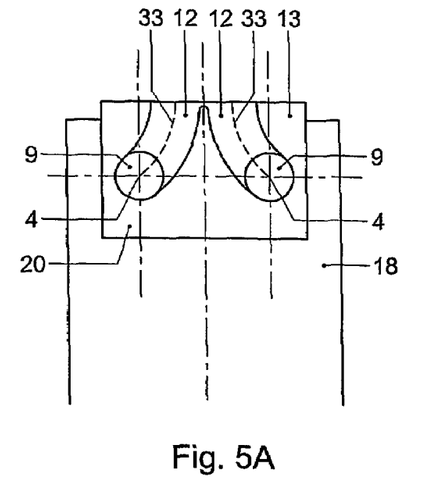
FIGS. 5a-d top plan views of alternative embodiments for an intermediate plate for a breath actuated dry powder inhaler having twin parallel circulation chambers.
Figure 5B:
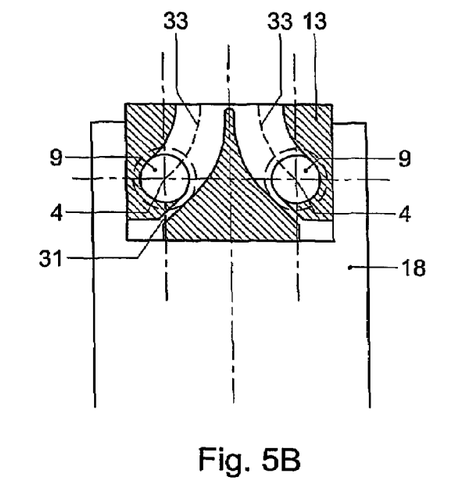
Figure 5C:
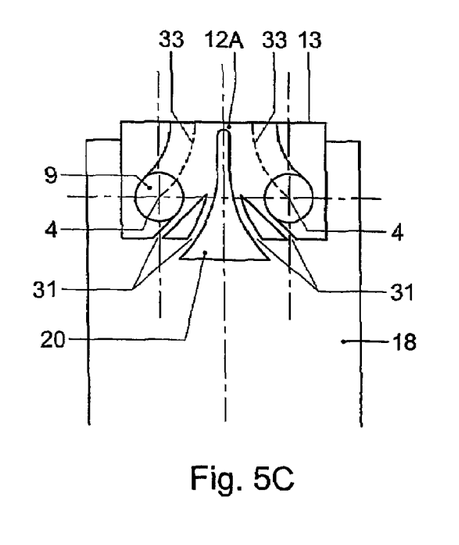
Figure 5D:
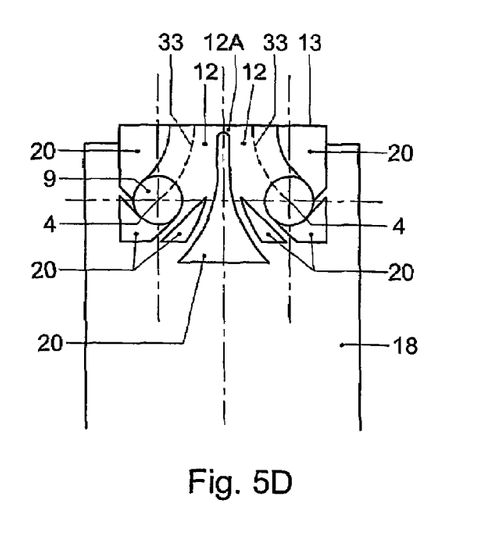
Figure 6A:
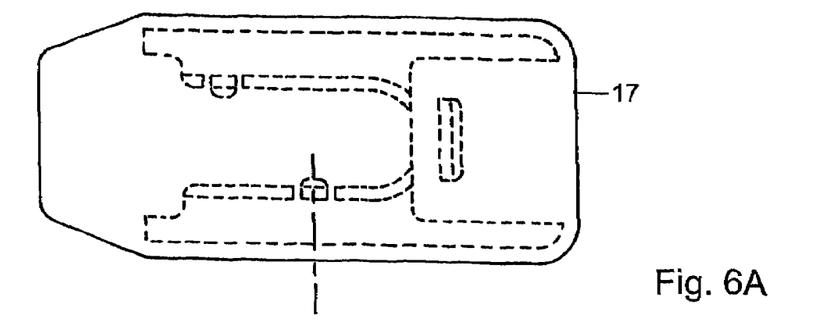
FIGS. 6a-c top plan views of respectively a top plate, an intermediate plate and a bottom plate for a the breath actuated dry powder inhaler having triple parallel circulation chambers.
Figure 6B:
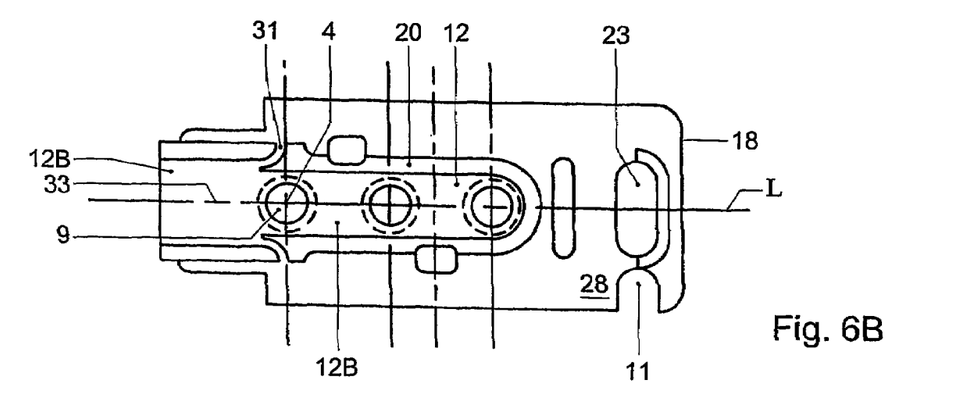
Figure 6C:
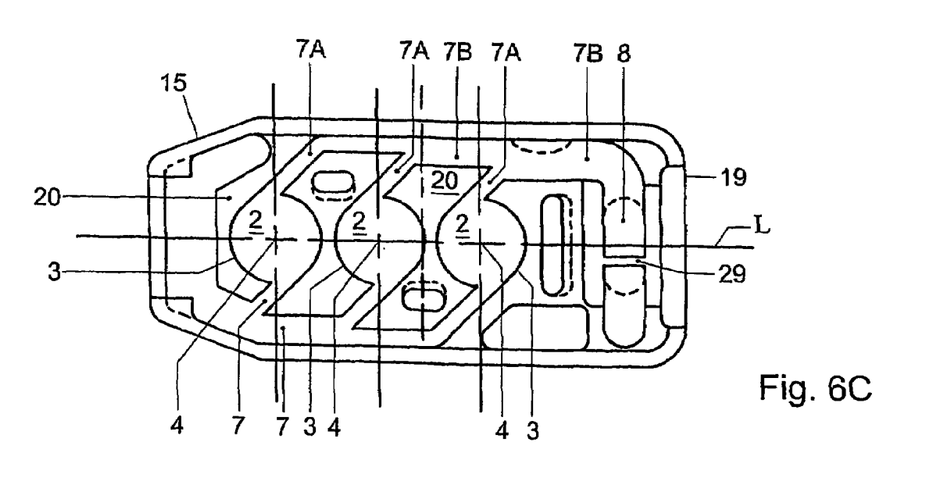
Figure 7A:
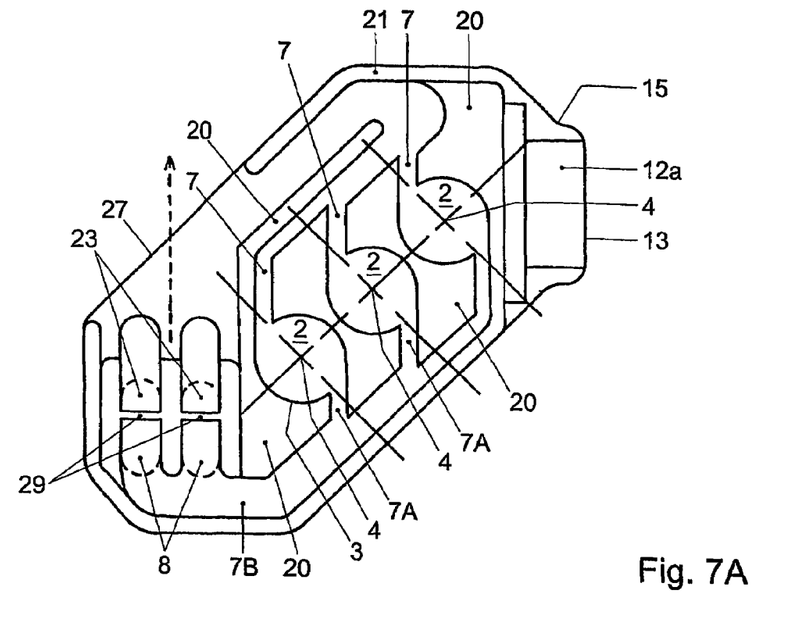
FIGS. 7a and b top plan views of alternative embodiments for a bottom plate for the inhaler of FIG. 6.
Figure 7B:
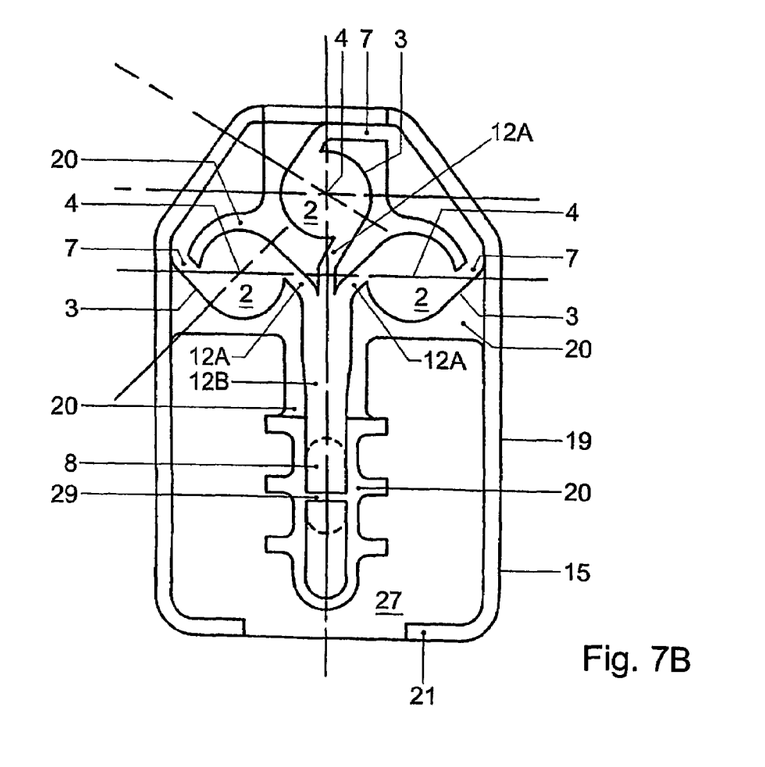
Figure 8:
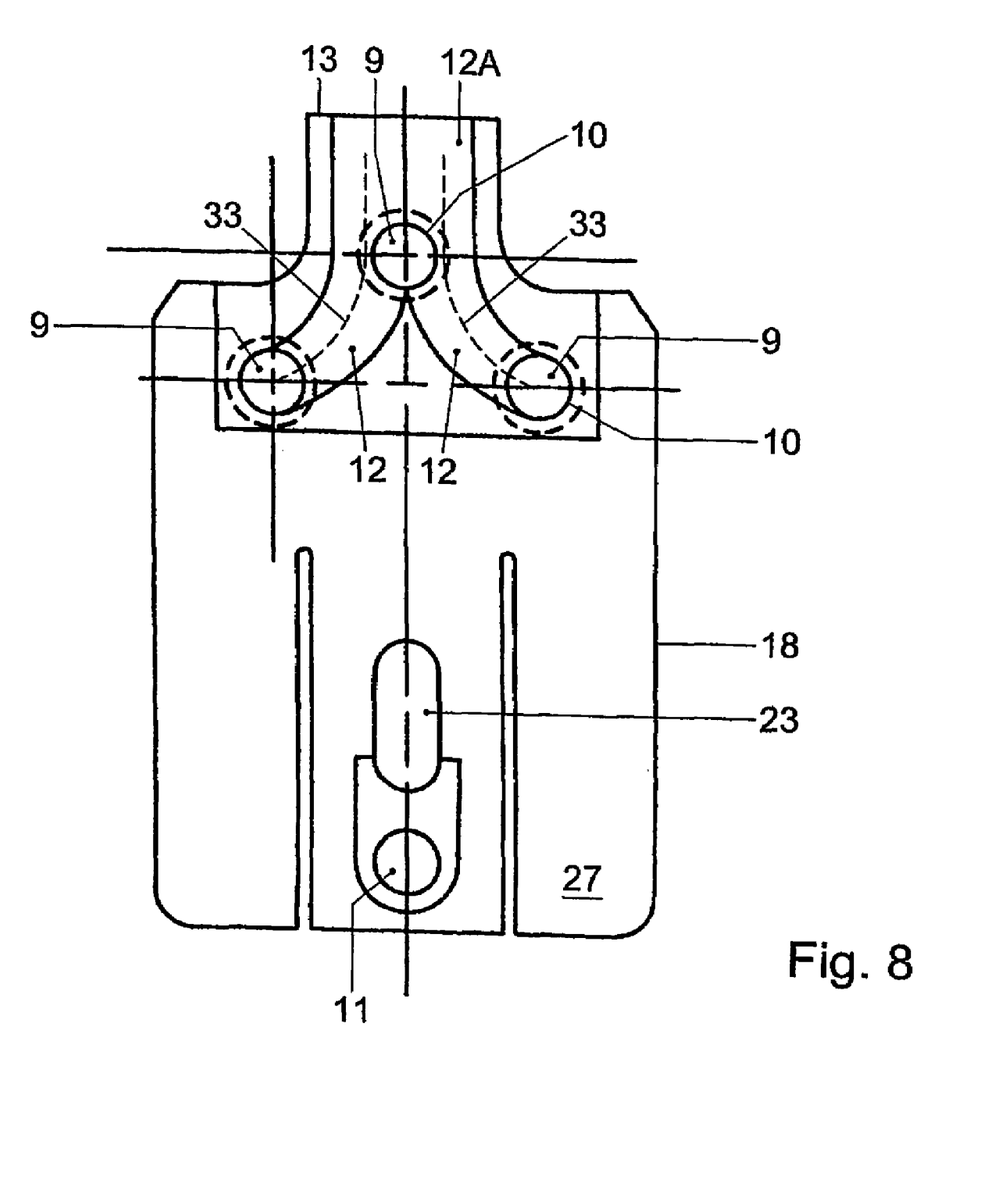
FIG. 8 a top plan view of an intermediate plate for the inhaler of FIG. 7b.
Figures 9A, 9B, 9C:
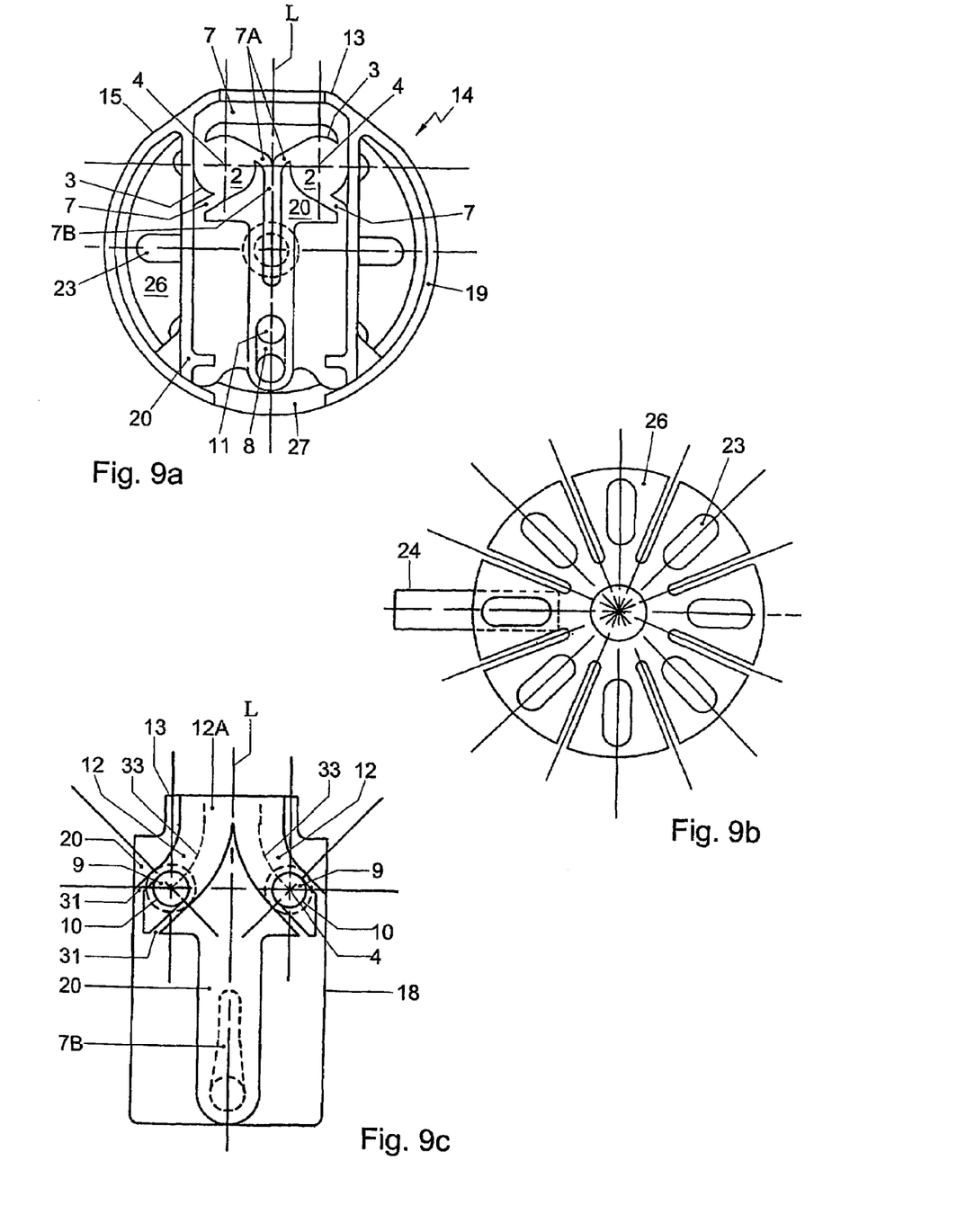

A plurality of blister pockets 23 comprising a single dose or a single therapy may e.g. be arranged in a row on a rectangular blister strip or in a circular arrangement on a round blister disk or a sector of a round disk as shown in FIGS. 9, wherein the blister pockets can e.g. be opened simultaneously or subsequently.

FIG. 9a shows a top plan view of a disc shaped embodiment of the breath actuated dry powder inhaler 1, comprising a carrier 26 carrying a plurality of sealed dose compartments 23, the compartments on the carrier 26 being indexable relative to the supply area 8 of the inhaler 1. The embodiment comprises a disc shaped top plate (not shown) forming a cover and carrying a mouth piece (not shown), which top plate covers the intermediate plate 18 shown in FIG. 9c that in turn is mounted onto the bottom plate 19 shown in FIG. 9a. The carrier 26 is formed by a disposable disc shaped blister on which blister pockets 23 are arranged in a circle. The blister 26 is indexably mounted on a central axis protruding from the bottom side of the bottom plate 19.

Figure 10:
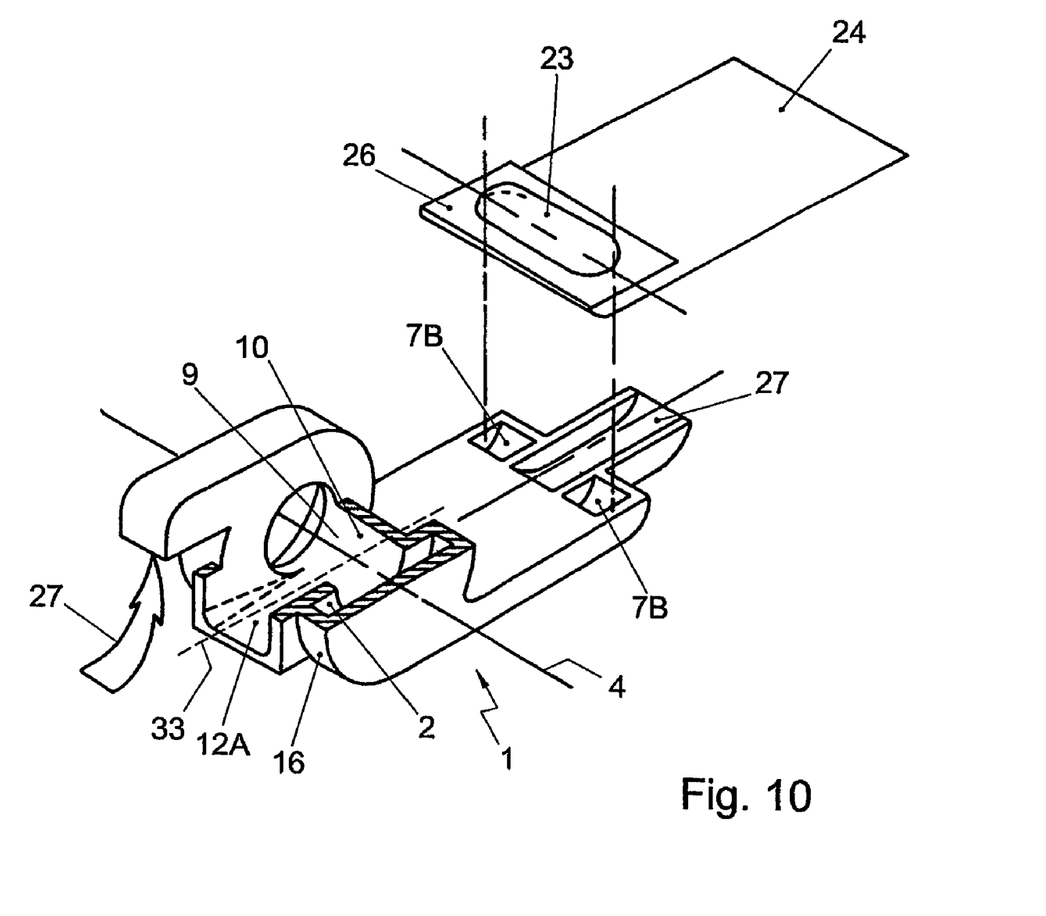
FIG. 10 a perspective view of yet another embodiment of an inhaler having facing twin circulation chambers.

As shown in the above figures, the classifying cambers 2 are arranged side-to-side in the same plane, having different parallel longitudinal axes 4. However, it is also possible to arrange the chambers 2 bottom-to-bottom, sharing the same axis. Also, it is possible to arrange the classifying chambers 2 top-to-top with their discharge holes 10 facing each other, sharing the same axis 4. Such an arrangement is shown in FIG. 10. From FIG. 10 it will be apparent that the chambers 2 need not be orientated with their axis 4 substantially vertically during use, but may e.g. also be orientated with their axes 4 substantially horizontally or obliquely. Further, the orientation of the classifying chambers need not be the same for all chambers.

These and other variations will be clear to the skilled man and are the scope of the invention as defied in the appended claims.

The invention claimed is:

1. A breath actuated dry powder inhaler, comprising a plurality of substantially disc shaped air circulation chambers for de-agglomeration of entrained powdered medicament using energy of an inspiratory air stream created by the user, the each of the chambers having a substantially circular or polygonal sidewall extending about a central axis between top and bottom walls of each of the chambers so that a height of each of the chambers is smaller than its diameter, a plurality of air supply channels disposed about a circumference of each of the chambers, which channels extend from joint or separate air inlets and which channels enter each of the chambers substantially tangentially to its sidewall, at least one of the supply channels extending through a powder dose supply region of the inhaler, each of the chambers further comprising an air outlet axially extending from a discharge opening in the center of the top or bottom wall of each of the chambers and connecting to a discharge channel that extends to a mouthpiece, said powder traveling through said dose supply region, then through a plurality of the air supply channels to one of said chambers and exiting through said discharge openings and air outlets, to the discharge channel and to the mouthpiece.

2. The breath actuated dry powder inhaler of claim 1, comprising a substantially planar housing, at least one chamber being disposed in the housing such that the central axis of the chamber extends transversely to a plane of the housing and the discharge channel being disposed in the housing such that it extends in the plane of the housing.

3. The breath actuated dry powder inhaler of claim 2, wherein the mouthpiece is provided on an edge of the housing.

4. The breath actuated dry powder inhaler according to claim 1, wherein the discharge channel and at least one circulation chamber extend in substantially parallel planes.

5. The breath actuated dry powder inhaler according to claim 1, wherein the housing is built up of a stack of planar elements.

6. The breath actuated dry powder inhaler according to claim 1, wherein the discharge channel connects substantially transversely to the air outlet of the chamber.

7. The breath actuated dry powder inhaler according to claim 1, wherein the circulation chambers are substantially similar.

8. The breath actuated dry powder inhaler according to claim 1, wherein the plurality of chambers are connected to a joint powder dose supply region.

9. The breath actuated dry powder inhaler according to claim 1, wherein at least two of the chambers are disposed in a same plane.

10. The breath actuated dry powder inhaler according to claim 1, wherein at least two of the chambers are disposed in parallel planes.

11. The breath actuated dry powder inhaler according to claim 10, wherein a joint or separate discharge channels are disposed in a further plane, disposed between the parallel planes.

12. The breath actuated dry powder inhaler according to claim 1, comprising a housing constructed as a disposable unit.

13. The breath actuated dry powder inhaler according to claim 1, wherein the dose supply region is formed by a sealed dose compartment containing a pre measured dose of powdered medicament, the dose compartment being included in the supply channel and blocking air passage through the channel until removal of the seal of the dose compartment.

14. The breath actuated dry powder inhaler according to claim 1, wherein a sealed dose compartment is a blister pocket sealed with a removable cover foil.

15. The breath actuated dry powder inhaler according claim 1, further comprising a carrier carrying a plurality of sealed dose compartments, the compartments on the carrier being indexable relative to the supply region of the inhaler.

16. A device for pulmonary inhalation, wherein dry powder medicament is inhaled from an inhaler through parallel air supply channels to a plurality of substantially disc shaped air-circulation chambers arranged in parallel and wherein the dry powder is de-agglomerated in the substantially disc shaped air-circulation chambers in the inhaler using energy of an inspiratory air stream created by a user, and wherein, under the action of the inspiratory air stream, the de-agglomerated medicament is axially discharged from the circulation chambers and is subsequently fed through parallel discharge openings and air outlets, to discharge channels towards a mouthpiece.

* * * * *

UNITED STATES PATENT AND TRADEMARK OFFICE
CERTIFICATE OF CORRECTION

| | | |
|---|---|---|
| PATENT NO. | : 7,617,822 B2 | Page 1 of 1 |
| APPLICATION NO. | : 10/561410 | |
| DATED | : November 17, 2009 | |
| INVENTOR(S) | : De Boer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 860 days.

Signed and Sealed this

Fourteenth Day of December, 2010

David J. Kappos
*Director of the United States Patent and Trademark Office*